US008251687B2

(12) United States Patent
Bertholdt

(10) Patent No.: US 8,251,687 B2
(45) Date of Patent: Aug. 28, 2012

(54) PROCESS FOR THE PRODUCTION OF A LONG HOLLOW CELLULOSE BODY

(75) Inventor: Günter Bertholdt, Heiningen (DE)

(73) Assignee: Bioregeneration GmbH, Garching (DE)

(*) Notice: Subject to any disclaimer, the term of this patent is extended or adjusted under 35 U.S.C. 154(b) by 1044 days.

(21) Appl. No.: 12/279,060

(22) PCT Filed: Feb. 19, 2007

(86) PCT No.: PCT/EP2007/001423
§ 371 (c)(1),
(2), (4) Date: Aug. 12, 2008

(87) PCT Pub. No.: WO2007/093445
PCT Pub. Date: Aug. 23, 2007

(65) Prior Publication Data
US 2009/0011161 A1    Jan. 8, 2009

(30) Foreign Application Priority Data

Feb. 19, 2006   (DE) .......................... 10 2006 007 412

(51) Int. Cl.
| A23G 1/22 | (2006.01) |
| A23G 3/12 | (2006.01) |
| A23G 3/16 | (2006.01) |
| B21C 3/00 | (2006.01) |
| A23P 1/00 | (2006.01) |
| B32B 3/10 | (2006.01) |
| B32B 19/00 | (2006.01) |
| B32B 23/00 | (2006.01) |

(52) U.S. Cl. ...................................... 425/117; 435/395

(58) Field of Classification Search .................. 435/101, 435/395, 252.3; 425/117
See application file for complete search history.

(56) References Cited

U.S. PATENT DOCUMENTS

2003/0013163 A1 * 1/2003 Klemm et al. ............... 435/101

FOREIGN PATENT DOCUMENTS

| CN | 1401005 | 3/2003 |
| EP | 0 186 495 | 7/1986 |
| EP | 0 396 344 | 11/1990 |
| JP | 63 205 109 | 8/1988 |
| JP | 03 165774 | 7/1991 |
| JP | 03 272772 | 12/1991 |
| JP | 08 126697 | 5/1996 |
| JP | 2005-320 657 | 11/2005 |
| WO | WO 00/23516 | 4/2000 |

(Continued)

OTHER PUBLICATIONS

S. Hestrin, M. Schramm: "Synthesis of Cellulose by Acetobacter Xylinum", Hebrew University Hadassah Medical School, Jerusalem, Israel, 1954.

(Continued)

Primary Examiner — Michael C Miggins

(57) ABSTRACT

Process for the production of a long hollow cellulose body, where cellulose-forming organisms are cultivated in an interior space formed by a hollow mold, said space substantially having the shape of the long hollow body, in order to allow the long hollow body to grow in the interior space, wherein the direction of growth of the hollow body runs substantially from a first longitudinal side of the interior space to a second longitudinal side substantially opposite the first.

5 Claims, 2 Drawing Sheets

FOREIGN PATENT DOCUMENTS

| WO | WO 01/61026 | 8/2001 |
|---|---|---|
| WO | WO 2004/045 458 | 6/2004 |

OTHER PUBLICATIONS

Forng et al.: "Synthetic Medium for Acetobacter Xylinum That Can Be Used for Isolation of Auxotrophic Mutants and Study of Cellulose Biosynthesis", Applied and Environmental Microbiology, vol. 55, No. 5, 1989, pp. 1317-1319.

English translation of the first Office Action of Chinese Patent Application No. 200780005110.5.

D. Klemm, D. Schumann, U. Udhardt, S. Marsch: "Bacterial synthesized cellulose—artificial blood vessels for microsurgery" Progress in Polymer Science, vol. 26, No. 9, 2001, pp. 1561-1603.

International Search Report and Written Opinion of PCT/EP2007/001423.

\* cited by examiner

PROCESS FOR THE PRODUCTION OF A LONG HOLLOW CELLULOSE BODY

BACKGROUND OF THE INVENTION

The invention relates to a process for the production of a long hollow cellulose body. It also relates to the long hollow body produced by the process.

STATE OF THE ART

At the present time the replacement of animal and human blood vessels is usually effected with tubes made of polyester or expanded PTFE. These artificial vessels have a limited life as functioning implants and only remain open for a period of a few months to a few years, even when the vessel diameter is larger than 5 millimeters. Below a diameter of 5 millimeters, it has only been possible hitherto to use endogenous material, with its associated disadvantages.

WO 01/61026 A1 describes the production of a microvascular prosthesis from microbial cellulose which has an internal diameter of 0.8 millimeter and, when used in the carotid artery of the rat, did not lead to any thrombogenesis, even after one month.

For the production of this hollow body, a glass matrix was described which consisted of a glass tube and an internal round glass rod fixed with O-rings, said matrix being vertically immersed in an inoculated nutrient solution. A nutrient solution inoculated with cellulose-producing bacteria can enter the space between the glass tube and the glass rod through an aperture in the lower part. Another aperture in the upper part creates an aerobic atmosphere that favours the cultivation of the bacteria, resulting in the deposition of cellulose. The hollow cellulose body grows symmetrically around the glass rod in the direction of the longitudinal axis of the hollow-cylindrical interior space created by the glass matrix.

A disadvantage of the known process is that vessels can only be produced in this way up to a length of 15 to 20 millimeters.

Problem on which the Invention is Based

The object of the invention is to provide an improved process for the production of a long hollow cellulose body, an improved long hollow cellulose body, and an improved hollow mould for the production of the long hollow cellulose body.

Solution According to the Invention

One aspect of the invention is that it dispenses with the rotational symmetry around the cylindrical axis of a hollow-cylindrical interior space, as known from the prior art. One aspect of the invention is that the hollow cellulose body grows not along the longitudinal axis of the interior space but substantially perpendicularly thereto. This means that the length of the hollow body is no longer limited by the layer thickness which can be achieved in the direction of growth.

An achievable advantage of the invention is that long hollow cellulose bodies of greater length can be produced. It is conceivable, in principle, to produce hollow cellulose bodies of any desired length.

An achievable advantage of the invention is that the hollow body can be produced more rapidly.

An achievable advantage of the invention is that it makes it possible to produce long hollow cellulose bodies which have a longer life as implants for organisms.

It is an achievable advantage of the invention that long hollow cellulose bodies can be produced, as implants for organisms, which are rejected or encapsulated less by the implant recipient's body.

It is an achievable advantage of the invention that long hollow cellulose bodies can be produced, as replacement vessels, which are less susceptible to the adhesion of thrombi.

The hollow cellulose bodies according to the invention can be used e.g. as implants for organisms, preferably mammals and particularly preferably humans, preferably for applications in vascular surgery and particularly preferably for the replacement of blood vessels, for the replacement of other internal hollow organs or as a sheath for encasing nerve fibres.

STRUCTURE AND DEVELOPMENT OF THE SOLUTION ACCORDING TO THE INVENTION

The long hollow body is preferably tubular and particularly preferably of substantially annular cross-section. Examples of other conceivable shapes are a long hollow barrel, a long frustum, a long bottle-shaped body or a long hollow ellipsoid. Preferred long hollow bodies have rotational symmetry around their longitudinal axis. An important departure from this consists of long hollow bodies with branches, which can also be produced by the process described and can be particularly appropriate for use as replacement blood vessels.

The long hollow bodies generally have longitudinal sides that extend from one end to the opposite end in the direction of the longitudinal axis of the hollow body.

Preferably, the hollow mould comprises a tube containing a circular rod positioned in the middle. The hollow mould preferably has one or more apertures on two opposite longitudinal sides. The aperture(s) preferably extends (extend) parallel to the longitudinal axis of the hollow body, particularly preferably over at least part of the length of the interior space in the shape of the hollow body, and very particularly preferably over substantially the whole length. The apertures can have a variety of shapes, either regular or irregular, an example being a row of holes like a perforation. The holes can be arranged in a regular or irregular manner. However, longitudinal through-slots are preferred. These longitudinal slots have a width preferably of between 0.2 and 4 millimeters and particularly preferably of 1-2 millimeters, depending on the tube diameter. In the case of a longitudinal through-slot, the two parts of the tube are preferably held together at the ends by thin bands, e.g. made of Teflon, or O-rings. The circular rod is preferably held in position by hollow-cylindrical objects, e.g. O-rings or short Teflon tubes, that fit closely, i.e. seal off the space between the circular rod and the inside of the hollow body.

The tube and the circular rod are preferably acid-resistant and particularly preferably made of a material that is chemically inert towards the substance and organisms used and/or formed in carrying out the process. Transparent materials, e.g. glass, are preferred. Generally inert materials are particularly preferred.

Preferably, the first step is to inoculate a nutrient solution, outside the hollow mould, with the cellulose-forming organism. The cellulose is preferably microbial cellulose. Cellulose produced e.g. by the bacterium *Acetobacter xylinus* is initially less dense and of lower strength, so it is preferable to wait until a sufficiently dense layer of cellulose has been deposited on the nutrient medium. This normally occurs after approx. 7-10 days.

In one preferred embodiment of the invention, the hollow mould is placed horizontally with the lateral aperture(s) on a growing layer of cellulose-producing bacteria. As the density of the cellulose is roughly the same as that of the nutrient medium, the cellulose layer is preferably supported, e.g. by a reticular object made of Teflon or glass.

The hollow body preferably grows in a direction perpendicular to the longitudinal axis of the interior space, and particularly preferably from bottom to top. In one preferred embodiment of the invention, the bacteria pass into the hollow mould through one or more lower apertures therein, in order to fill it with cellulose, it being possible at the same time for liquid medium to diffuse a short distance onto the cellulose surface in order to supply the bacteria.

Oxygen is supplied through one or more upper apertures in the hollow mould. As soon as cellulose emerges through the upper aperture(s), the mould can be opened and the hollow cellulose body removed; in the case of a hollow mould with a hollow-cylindrical interior space, the product formed is a cylindrical hollow body.

Preferably, the hollow body is then cleaned. Particularly preferably, the bacteria still present in this hollow cellulose body are removed by boiling for 10 minutes in 0.1 N sodium hydroxide solution.

In the case where the type with longitudinal slots is used, the hollow body can have, on two opposite sides, projections each in the shape of a narrow ridge, comb or fin. The first and second projections or rows of projections extend preferably over most of the length of the hollow cylinder, and particularly preferably over substantially the whole length. They preferably run substantially parallel to the cylindrical axis of the hollow cylinder. It is an achievable advantage of this embodiment of the invention that, when used as a vascular prosthesis, the comb facilitates handling of the prosthesis with surgical instruments, e.g. forceps, without the prosthesis being damaged. It is another achievable advantage of this embodiment of the invention that the comb can serve as a subsidiary line for indicating a disadvantageous twisting of the prosthesis, especially in cases of tissue tunnelling.

The cellulose-forming organisms are preferably bacteria and particularly preferably those of the *Acetobacter xylinus* strain.

A variety of nutrient media are described for the cultivation of *Acetobacter xylinus*. A suitable, frequently used medium is the Schramm and Hestrin medium described in Biochemical Journal 1954, 58, pages 345-352. The entire relevant content of the article cited above is incorporated in the present disclosure by reference. A possible disadvantage of this medium is that it is not precisely defined, since it contains yeast extract and peptone.

The present invention is preferably carried out using a fully synthetic medium such as that described e.g. by Forng et al. in Applied and Environmental Microbiology 1989, volume 55, number 5, pages 1317-1319. The entire relevant content of the article cited above is incorporated in the present disclosure by reference. A possible disadvantage of this medium is the somewhat slower growth of the bacteria.

It is also conceivable to carry out the invention using the so-called Kombucha tea fungus. Apart from *Acetobacter xylinus*, this culture contains numerous other organisms living in symbiosis, such as yeasts and bacteria, and can be maintained by a medium consisting solely of black tea and sucrose (100 grams/liter).

BRIEF DESCRIPTION OF THE DRAWINGS

The invention is illustrated in greater detail below with the aid of schematic drawings of embodiments.

DESCRIPTION WITH THE AID OF EMBODIMENT

Figure 1:
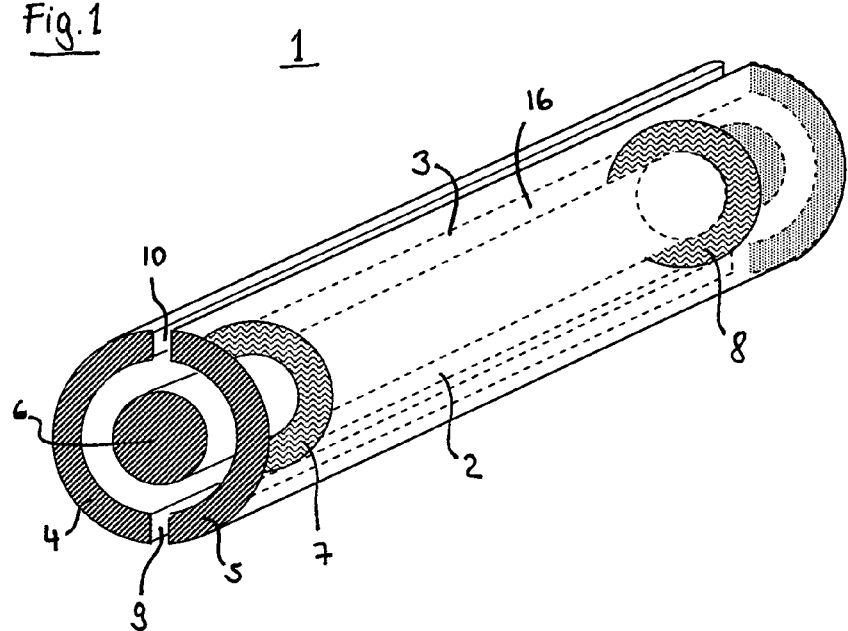
FIG. 1: is a schematic perspective of a first hollow mould according to the invention.
Figure 2:
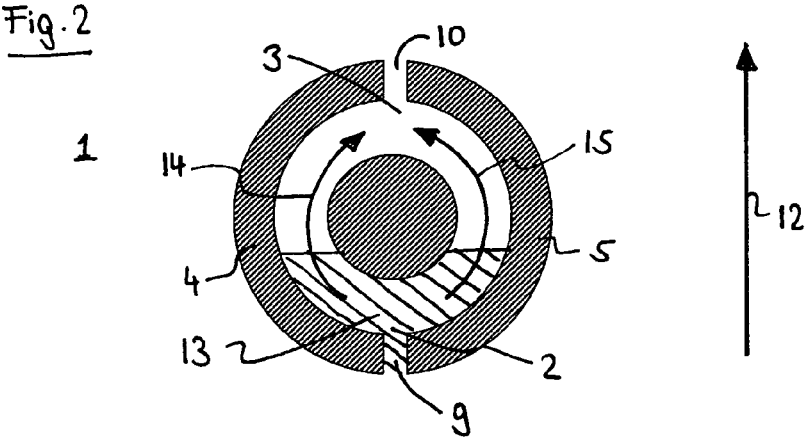
FIG. 2: is a schematic cross-section of an incompletely grown, long hollow body in the hollow mould, showing the direction of growth.
Figure 3:
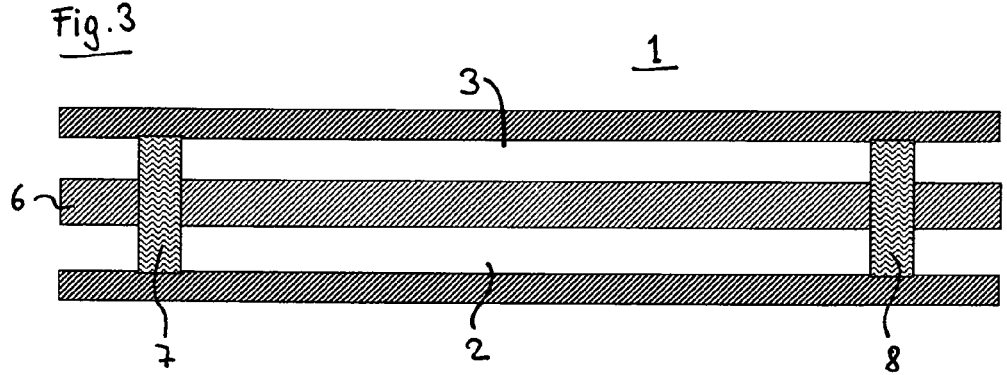
FIG. 3: is a schematic longitudinal section of the first hollow mould according to the invention.

The hollow mould 1 shown in FIGS. 1 to 3 has an interior space in the shape of a hollow cylinder with two annular ends and longitudinal sides 2 and 3. This interior space is formed by two glass half-tubes 4, 5, a circular glass rod 6 and two O-rings 7, 8. Slot-shaped apertures 9, 10, which run between the half-tubes over the whole length of the hollow mould, provide external access to the interior space 16 of the hollow mould 1.

As shown in FIG. 2, the hollow cellulose body 11 grows inside the interior space 16 of the hollow mould 1 in the general direction indicated by the arrow 12, perpendicularly to the longitudinal axis of the interior space, from one longitudinal side 2 to the other longitudinal side 3.

More precisely, the cellulose grows initially through an aperture 13 in the hollow mould 1 on the first longitudinal side 2 into the hollow mould 1, and then along the arrows 14, 15 to the other longitudinal side 3. At the same time, an exchange of air with the surroundings of the hollow mould 1 can take place via a second aperture 10, in particular to supply the organisms with oxygen. Through the apertures 9 the cellulose can transport the necessary nutrients from the growth medium outside to the organisms inside the hollow mould. Finally, the cellulose grows into the aperture 10.

Example 1

Figure 4:
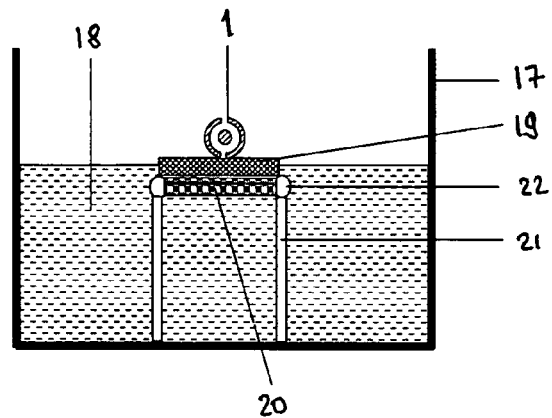
FIG. 4: is a schematic cross-section of a structure for carrying out the process according to the invention.

As shown schematically in FIG. 4, a sterile vessel 17 with a capacity of 2000 milliliters is filled with 1000 milliliters of a sterile nutrient solution 18 consisting of 20 grams of glucose, 5 grams of yeast extract, 5 grams of bactopeptone, 2.7 grams of sodium phosphate and 1.15 grams of citric acid monohydrate, pH 6.0, and inoculated with a 3-day-old pre-culture of *Acetobacter xylinus* (e.g. *Gluconacetobacter xylinus*, DSM no. 6513, DSZM Brunswick). After approx. 7 days, when a cellulose layer 19 about 3 millimeters thick has formed on the liquid surface, it is supported by a Teflon mesh 20 (ePTFE, expanded polytetrafluoroethylene, e.g. GLIDE dental floss, W.L. GORE & Associates Inc.) mounted in a glass frame 22 carried by glass supports 21.

Two glass tubes (Duran glass, internal diameter 6 millimeters, wall thickness 1.5 millimeters, length 150 millimeters) are sawn through in the longitudinal direction to give two parts 4, 5, which, with the cut edges placed on top of one another, make a height of approx. 7 millimeters. These two glass tube parts 4, 5 are then positioned symmetrically around a glass rod 8 (Duran glass, diameter 3 millimeters, length 150 millimeters), which is fitted at each end with a vulcanized rubber O-ring 7, 8 (internal diameter 3 millimeters, wall thickness 1.5 millimeters), and fastened at the ends with a Teflon thread (GLIDE dental floss, W.L. GORE & Associates Inc.). The resulting hollow mould 1, which has an approx. 2 millimeter wide through-slot 9, 10 on two sides, is placed, with a slot 9 facing downwards, on the cellulose surface supported by a mesh 20, and cultivated at 28° C. in an incubator. It generally takes 2 to 3 weeks for the hollow mould 1 to be colonized by the bacteria and filled with cellulose. During this time, care must be taken to ensure that consumed or evaporated medium 18 is replaced if necessary. When the hollow mould 1 is completely full of cellulose, it can be opened and the hollow cellulose body formed can be removed. The bacteria still present in the hollow cellulose body are killed by boiling for 10 minutes in 0.1 N NaOH, and removed.

Example 2

Approx. 2 liters of boiling water are poured over approx. 20 grams of black tea (Paul Schrader China "Naturbelassen", no. 400) and left to stand for 15 minutes. 200 grams of sucrose (Südzucker) are then dissolved in the tea. After cooling, the tea is transferred to a culture vessel 17 with a capacity of approx. 4000 milliliters (length 40 centimeters, height 10 centimeters, width 10 centimeters). A slice of a preculture of Kombucha "tea fungus" (e.g. Vukovits International, 91522 Ansbach) of diameter approx. 10 centimeters and thickness approx. 15 millimeters is placed in the culture vessel 17 together with approx. 155 milliliters of preculture medium and cultivated at 28° C. After about 7 days an approx. 3 millimeter thick cellulose layer 19 has formed on the liquid surface and is supported by a mesh 20 of ePTFE threads (GLIDE dental floss, W.L. GORE & Associates Inc.) mounted in a glass frame 22 carried by glass supports 21.

Figure 5:
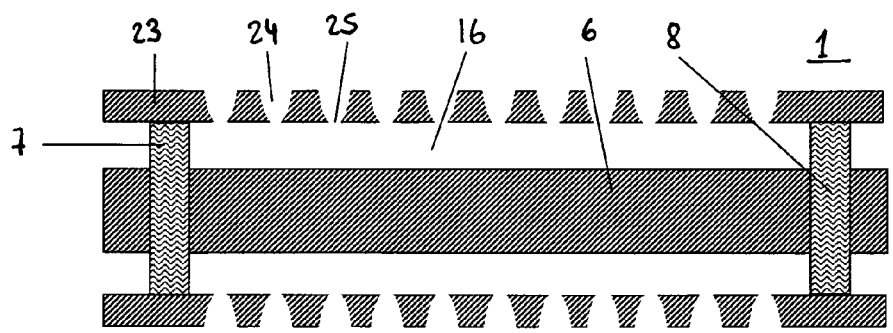
FIG. 5: is a schematic longitudinal section of a second hollow mould according to the invention.
Figure 6:
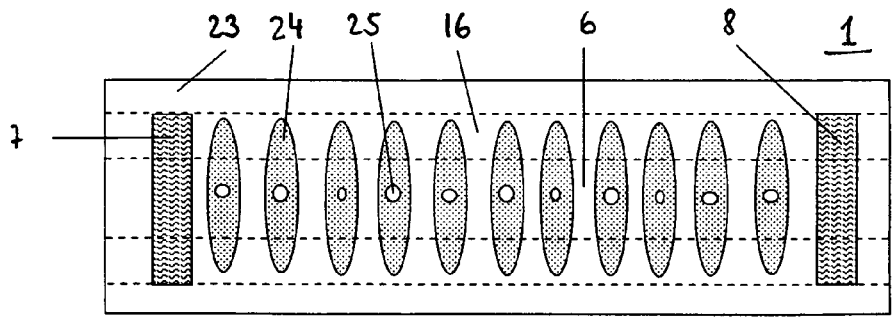
FIG. 6: is a schematic overhead view of the second hollow mould according to the invention.

As shown in FIGS. 5 and 6, a glass tube 23 (Duran glass, internal diameter 6 millimeters, wall thickness 2 millimeters, length 300 millimeters) is sawn radially, with the formation of slits 24, so that the tube wall is just cut through to form a roughly circular aperture 25 with a radius of 2 to 3 millimeters. This process is repeated in a line in the longitudinal direction, at intervals of 4 to 5 millimeters, to give a row of holes resembling a perforation. Another row of holes is produced on the opposite side by the same procedure. In the middle of this tube perforated on both sides, a glass rod 6 (Duran glass, diameter 3 millimeters, length 300 millimeters) is fixed at the ends by means of vulcanized rubber O-rings 7, 8 (internal diameter 3 millimeters, wall thickness 1.5 millimeters). With one row of holes facing downwards, the resulting hollow mould 1 is placed on the cellulose surface supported by a mesh 20, and cultivated at 28° C. until the hollow mould 1 is completely full of cellulose. During this time, care must be taken to ensure that consumed or evaporated medium 18 is replaced (e.g. from the preculture). The hollow cellulose body formed is removed by being carefully pushed out, the thin connections to the perforations being simultaneously cut away by the sharp glass edges to form a hollow cylinder without a ridge. The bacteria still present therein are killed by boiling for 10 minutes in 0.1 N NaOH, and removed.

The invention claimed is:

1. A process for the production of a long hollow cellulose body, where cellulose-forming organisms are cultivated in an interior space formed by a hollow mould, said space substantially having the shape of the long hollow body, in order to allow the long hollow body to grow in the interior space, Wherein the direction of growth of the hollow body runs substantially from a first longitudinal side of the interior space to a second longitudinal side substantially opposite the first.

2. The process according to claim 1, wherein the cellulose grows into the interior space from outside through at least one first aperture present in the hollow mould, the first aperture being located on the first longitudinal side of the interior space in the shape of the hollow body.

3. The process according to claim 1, wherein a gas or mixture of gases is exchanged between the interior space and the surroundings of the hollow mould via at least one second aperture in the hollow mould, the second aperture being located in such a way that the organisms are supplied substantially throughout the growth process with the gases necessary for growth of the cellulose.

4. A long hollow cellulose body produced by the process described in claim 1.

5. The long hollow cellulose body according to claim 4, comprising one or more branches.

* * * * *